United States Patent [19]

Laurenzo

[11] Patent Number: 4,931,596
[45] Date of Patent: * Jun. 5, 1990

[54] PROCESS FOR PREPARING HYDROXYLATED AMINES

[75] Inventor: Kathleen S. Laurenzo, Baton Rouge, La.

[73] Assignee: Ethyl Corporation, Richmond, Va.

[*] Notice: The portion of the term of this patent subsequent to Dec. 19, 2006 has been disclaimed.

[21] Appl. No.: 292,831

[22] Filed: Jan. 3, 1989

[51] Int. Cl.$^5$ ............... C07C 213/03; C07C 321/14; C07C 215/08; C07C 269/04

[52] U.S. Cl. ..................... 564/477; 564/475; 564/501; 564/503; 562/555

[58] Field of Search ............. 564/475, 477, 503, 501; 562/555; 260/501.11, 501.12

[56] References Cited

U.S. PATENT DOCUMENTS 3,047,066 7/1962 Mosely ..................... 166/32
4,196,217 4/1980 Rancurel et al. ............ 424/316

OTHER PUBLICATIONS

U.S. Ser. No. 269,363 entitled "Substituted Ammonium Carbamates and Method for Preparing Same" filed Nov. 10, 1988, 15 pages.

Primary Examiner—Richard L. Raymond
Assistant Examiner—P. O'Sullivan
Attorney, Agent, or Firm—W. G. Montgomery; J. D. Odenweller

[57] ABSTRACT

Hydroxylated primary amines corresponding to the formula:

$$R-X-CH_2-CH(OH)-CH_2NH_2 \quad (I)$$

in which R is a saturated or unsaturated straight chain $C_5-C_{18}$ aliphatic radical and X represents $-O-$, $-S-$, $-NH-$ or $-CH_2-$ are prepared by reacting an epoxide of the formula:

$$R-X-CH_2-\underset{\underset{R_2}{|}}{CH}-CH_2R_1 \quad (II)$$

in which R and X are as defined previously and $R_1$ and $R_2$ together represent an epoxy radical with ammonium carbamate to form the corresponding substituted ammonium carbamate of the formula:

$$R-X-CH_2-CH(OH)-CH_2-NH-CO_2^- \quad (III)$$

$$R-X-CH_2-CH(OH)-CH_2-\overset{+}{N}H_3$$

in which R and X are as defined previously and thereafter heating the substituted ammonium carbamate thus formed at a temperature and for a length of time sufficient to form the corresponding hydroxylated primary amine of formula (I).

The hydroxylated primary amines of formula (I) and the salts of these compounds, particularly the hydrohalide, acetate and quaternary alkyl ammonium salts thereof are useful as medicaments, anticeptics, sterilizing agents and preservatives.

8 Claims, No Drawings

PROCESS FOR PREPARING HYDROXYLATED AMINES

BACKGROUND OF THE INVENTION

This invention relates to a novel process for the preparation of hydroxylated primary amines. More particularly, this invention relates to a novel process for the preparation of hydroxylated primary amines having the formula:

$$R-X-CH_2-CH(OH)-CH_2NH_2 \quad (I)$$

in which R represents a saturated or ethylenically or acetylenically unsaturated straight-chain $C_5$-$C_{18}$ aliphatic radical and X represents —O—, —S—, —NH— or —CH$_2$—, preferably an oxygen or sulfur atom and the hydrohalide, acetate and quaternary alkyl ammonium salts of these compounds. These compounds are known and are disclosed in Rancurel, et al, U.S. Pat. No. 4,196,217. The nonyl, decyl and dodecyl radicals are mentioned in particular as examples of a saturated aliphatic radical which may be represented by the radical R. These compounds, and particularly the compound of formula (I) in which R is the decyl radical and X is oxygen, i.e., 1-amino-3- decyloxy-2-propanol in the form of its hydrochloride, hydrobromide or acetate salt, are disclosed as being useful as sterilizing agents, preservatives and antiseptics.

Rancurel et al, U.S. Pat. No. 4,196,217, disclose that the compounds of formula (I) in which X is sulfur or oxygen can be prepared by the following process:

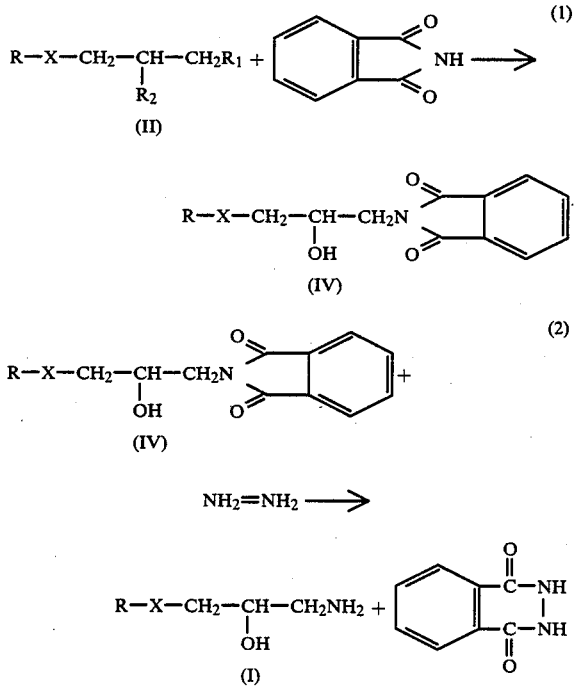

In these formulas, X represents —O— or —S—, R has the same meaning as in formula (I) and $R_1$ and $R_2$ together represent an epoxy radical or $R_2$ represents a hydroxy radical and $R_1$ is a halogen atom, preferably chlorine or bromine.

The reaction of equation (1) is carried out in the presence of a compound, such as potassium or sodium carbonate, which is capable of making the phthalimide react in the form of its sodium or potassium derivative.

The hydrolysis reaction (2) is carried out in the presence of hydrochloric acid.

The compounds of formula (II) are known compounds as are methods for their preparation and may be prepared, for example, by reacting an epihalohydrin:

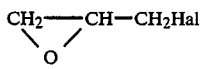

with an alcohol in the presence of a catalyst, such as stannic chloride, zinc chloride, ferric chloride, the boron fluoroetherate complex or tosylic acid. The product obtained is a halogenated alcohol.

The epoxide of formula (II) may be prepared by cyclizing the above halogenated alcohol or by other known methods.

Rancurel et al, in U.S. Pat. No. 4,196,217 also disclose that the compounds of formula (I) can be prepared by reacting ammonia or an amine such as triethylamine with a halogenated alcohol of formula (II) or with an epoxide of formula (II). However, Rancurel et al, state that these reactions generally result in the formation of a mixture of amines in addition to the desired primary amine. For example, when using ammonia, the primary amine product is a better nucleophile than ammonia and can compete effectively for starting material leading to the formation of secondary and tertiary amines in addition to the desired primary amine product. Similarly, the use of primary amines results in mixtures of secondary and tertiary amine products. This lack of selectivity makes these routes unattractive commercially. Further, production of the compounds of formula (I) by the Gabriel synthesis route disclosed by Rancurel et al involves the use of phthalimide which is expensive and hydrazine which is used to hydrolyze the first formed N-alkylphthalimide making this route not only commercially unattractive from the standpoint of cost but also dangerous due to the toxicity and potential explosiveness of hydrazine.

K. S. Laurenzo in U.S. Ser. No. 269,363 filed Nov. 10, 1988 discloses a method for preparing the hydrohalide and acetate salts of the hydroxylated amines of formula (I) in high yields and at reduced cost without the need for using costly phthalimide or potentially dangerous hydrazene by reacting an expoxide of formula (II) with ammonium carbamate to form the corresponding substituted ammonium carbamate and thereafter lU forming the corresponding hydrohalide or acetate salt of the substituted ammonium carbamate by conventional techniques such as, for example, by contacting the substituted ammonium carbamate with gaseous or aqueous hydrogen chloride or hydrogen bromide or, in the case of the acetate, reacting the substituted ammonium carbamate with acetic acid. This represents a substantial advance in the art.

SUMMARY OF THE INVENTION

In accordance with the present invention, it has now been discovered that the hydroxylated primary amines of formula (I) can also be produced in high yields and at reduced cost without the need for using costly phthalimide or potentially dangerous hydrazine. The process involves first reacting an epoxide of the formula:

$$R—X—CH_2—CH(R_2)—CH_2R_1 \quad (II)$$

in which R and X are as defined above and $R_1$ and $R_2$ together represent an epoxy radical with ammonium carbamate of the formula:

$$H_2NCO_2NH_4$$

to form the corresponding substituted ammonium carbamate having the formula:

$$R—X—CH_2—CH(OH)—CH_2—NH—CO_2^- \quad (III)$$

$$R—X—CH_2—CH(OH)—CH_2—\overset{+}{N}H_3$$

wherein R and X are as defined previously and thereafter heating the substituted ammonium carbamate thus formed at a temperature and for a length of time sufficient to form the corresponding hydroxylated primary amine of formula (I).

DESCRIPTION OF PREFERRED EMBODIMENTS

Thus, in accordance with one embodiment of the invention lU there is provided a novel process for preparing an hydroxylated primary amine corresponding to the formula:

$$R—X—CH_2—CH(OH)—CH_2NH_2 \quad (I)$$

in which R is a saturated or unsaturated straight claim $C_5$–$C_{18}$ aliphatic radical and X represents —C—, —S—, —NH— or —CH_2— by reacting a compound corresponding to the formula:

$$R—X—CH_2—CH(R_2)—CH_2R_1 \quad (II)$$

in which R and X are as defined previously and $R_1$ and $R_2$ together represent an epoxy radical with ammonium carbamate to form the corresponding substituted ammonium carbamate having the formula:

$$R—X—CH_2—CH(OH)—CH_2—NH—CO_2^- \quad (III)$$

$$R—X—CH_2—CH(OH)—CH_2—\overset{+}{N}H_3$$

in which R and X are as defined previously and thereafter heating the substituted ammonium carbamate thus formed at a temperature and for a length of time sufficient to form the corresponding hydroxylated primary amine of formula (I).

As disclosed in K. S. Laurenzo U.S. Ser. No. 269,363, reaction of the epoxide of formula (II) with ammonium carbamate to form the substituted ammonium carbamate of formula (III) in general is conducted at ambient temperature and pressure although elevated temperatures can be used if desired to afford a faster reaction rate. Temperatures ranging from ambient up to approximately 55° C. are useful temperatures at which to carry out the reaction. Higher temperatures can cause decomposition of the ammonium carbamate reactant as well as the substituted ammonium carbamate reaction product.

The reaction should be conducted for a time sufficient to achieve the desired degree of completion of the reaction. The reaction time is not a truly independent variable but is at least dependent to some extent on other process conditions employed. In general, higher temperatures should afford a faster reaction rate and, conversely, lower reaction temperatures should tend to decrease the rate of reaction. In general, the reaction time will be dependent to some degree on the choice of epoxide reactant used in the process and the type of equipment used. Good results are obtained in about 3 to 5 days, generally in about 4 to 5 days.

The amount of ammonium carbamate employed in the process should be at least a stoichiometric amount. This is 1 mole per mole of epoxide reactant. The ammonium carbamate is preferably used in excess in order to ensure maximum production of the desired substituted ammonium carbamate product. A preferred amount is about 1 to 10 moles of ammonium carbamate per mole of epoxide reactant. A more preferred amount is about 3 to 7 moles of ammonium carbamate per mole of epoxide reactant. A still more preferred amount is about 4 to 6 moles of ammonium carbamate per mole of epoxide reactant. Conveniently, any excess ammonium carbamate present at the completion of the reaction reverts to $NH_3$ and $CO_2$ during work up which is easily disposed of by passing the off-gases through an aqueous solution of an appropriate acid, such as hydrochloric acid to trap the $NH_3$ gas. The non-hazardous $CO_2$ passes through the solution unchanged.

The substituted ammonium carbamate is easily separated from the reaction mixture and purified by known methods such as liquid-solid extraction or fractional crystallization and is readily converted to the corresponding hydroxylated primary amine by simply heating the substituted ammonium carbamate at a temperature and for a length of time which is sufficient to convert the substituted ammonium carbamate to the hydroxylated primary amine product.

In general, it has been found that suitable temperatures range from about 50° C. up to about 100° C. with useful heating times varying from about 3 to 50 hours. Excellent results have been obtained by heating the substituted ammonium carbamate to a temperature of about 80° C. for about 24 hours. The substituted ammonium carbamate is unstable to heat and, when heat is applied to the carbamate, carbon dioxide is driven off leaving the free primary amine. Yields are essentially quantitative.

Advantageously, the reaction between the epoxide and ammonium carbamate reactants can be carried out in the presence of a lower alkanol as a reaction medium. Preferred alkanols have from 1 to 6 carbon atoms and no olefinic unsaturation. These preferred alkanols are methanol, ethanol, n-propanol, isopropanol, n-butanol, n-pentanol, n-hexanol and the like. Anhydrous methanol is preferred. Sufficient lower alkanol should be employed to produce a readily fluid reaction mixture. In general, an amount of alkanol ranging from about 0.1 to about 2 liters per mole of ammonium carbamate can be employed in the reaction.

The epoxide reactant used in the present process corresponding to the formula:

$$R—X—CH_2—CH(R_2)—CH_2R_1 \quad (II)$$

where R,R$_1$, R$_2$ and X are as defined previously are known compounds as are methods for their preparation. For example, they may be prepared by reacting an epichlorohydrin of the formula:

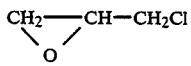

with an alcohol (ROH) where R is as defined as above in the presence of a catalyst, such as stannic chloride, zinc chloride, ferric chloride or tosylic acid to form the corresponding chlorinated alcohol of the formula:

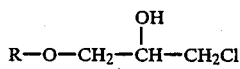

and cyclizing the alcohol to the epoxide by conventional means, e.g., by reaction with a slight excess of a base such as sodium hydroxide.

The ammonium carbamate reactant is readily prepared by known methods such as by directly combining ammonia and carbon dioxide in the gas phase and also in inert solvents such as absolute alcohol and petroleum ether.

If desired, the salts of the hydroxylated primary amine compounds made by the process of the present invention, particularly the hydrohalide salts such as the hydrochloride and hydrobromide salts thereof, as well as the acetates and alkylated quaternary ammonium derivatives thereof, can be easily prepared by conventional techniques such as reacting the hydroxylated primary amine compounds produced by the process of the present invention with gaseous or aqueous hydrogen chloride or hydrogen bromide, or in the case of the acetate by reacting the hydroxylated primary amine compound with acetic acid or in the case of an alkylated quaternary ammonium derivative by reacting the hydroxylated primary amine with an organohalide compound such as an alkyl halide, an alkenyl halide an arylakyl halide and the like.

The preparation of the compounds according to the invention is illustrated by, but by no means limited to, the following examples.

EXAMPLE 1

Preparation of 1-Chloro-3-Decyloxy-2-Propanol

Decanol (316 g, 2.0 mole) was charged to a 1000 ml three-necked round bottom flask equipped with a mechanical stirrer, thermometer, condenser and addition funnel, and stirred under N$_2$ atmosphere. SnCl$_4$ (3.79 ml, 0.02 mole, 1 mole %) was added and he mixture was heated to 80° C. Epichlorohydrin (185 g, 2.0 mole) was added dropwise over 55 minutes, at such a rate that the temperature did not exceed 100° C. After the addition was complete, the mixture was stirred at 100° C. for an additional 70 minutes. Analysis by GC (gas chromatography) showed the crude product contained 10% unreacted alcohol, and 76% of the desired 1-chloro-3-decyloxy-2-propanol.

EXAMPLE 2

Preparation of (Decyloxy)methyloxirane

To the crude 1-chloro-3-decyloxy-2-propanol prepared as described above and cooled to 40° C. was added NaOH (50% aqueous, 176 g, 2.2 mole) and water (44 g). The temperature rose to 50° C., then the mixture was heated to 85° C.–90° C. for three hours. Analysis by GC showed the crude product contained 11% unreacted alcohol and 75% of the expected epoxide. Water (200 ml) was added to dissolve precipitated salt. The aqueous phase was separated (pH 14) and the organic phase washed with 5% NaCl solution to pH 7–8 (2 ×400 ml). The crude product (435 g, 102%) was fractionally distilled at 12 mmHg to yield 286 g of (decyloxy)methyloxirane (67% overall based on epichlorohydrin). GC showed the product was 97% pure.

EXAMPLE 3.

Preparation of Ammonium Carbamate

Anhydrous ammonia was passed into a two liter four-necked round bottom flask chilled in a dry ice/acetone bath and equipped with thermometer, gas bubbler and calcium chloride drying tube, until approximately 150 ml liquid NH$_3$ was condensed. Powdered CO$_2$ was added at such a rate that the temperature did not exceed −60° C., until no further exotherm was observed. The temperature was allowed to rise slowly to ambient. The white solid residue was ammonium carbamate (276 g, 3.5 mole).

EXAMPLE 4

Preparation of 3-Decyloxy-2-Hydroxypropylcarbamic Acid. 3-Decyloxy-2-Hydroxypropylammonium Salt The ammonium carbamate prepared as described above was dissolved in anhydrous methanol (a total of 3.5 L) and transferred to a five liter three-necked round bottom flask equipped with thermometer and magnetic stirrer. (Decyloxy)methyloxirane (150 g, 0.7 mole) was added and the mixture was stirred at ambient temperature for five days, after which no more epoxide could be detected by TLC (silica gel, 4:1 hexane:methyl t-butyl ether, R$_f$=0.62). A small amount of precipitate was observed. The mixture was cooled to 5° C. and suction filtered on a coarse frit. After drying, 8.2 g of white solid was obtained. The methanol solution was evaporated to dryness on a rotary evaporator at about 5 mm Hg and a bath temperature of about 40° C. The crude substituted ammonium carbamate was obtained as a white solid (161 g, 91%).

The crude carbamate was washed with ether (3 ×300 ml) to yield 120.3 g (68%) purified product.

EXAMPLE 5

Conversion of 3-Decyloxy-2-hydroxypropylcarbamic acid, 3-Decyloxy-2-hydroxypropylammonium Salt to 1-Amino-3-decyloxy-2-propanol Thermal gravimetric analysis of the carbamate salt showed that above 55° C., weight loss ensued corresponding to the theoretical amount of CO$_2$ in the carbamate salt. A sample of carbamate prepared as described above (0.557 g) was heated at 80° C. for 24 hr. The white crystalline powder was converted to a light yellow oil which solidified on cooling to a pale waxy solid; yield 0.509 g (theory 0.5085). The material was identified by $^1$H and $^{13}$C nmr and IR spectra, physical appearance and solubility characteristics as being 1-amino-3-decyloxy-2-propanol.

I claim:

1. A process for preparing an hydroxylated primary amine corresponding to the formula:

   (I)

wherein R is a saturated or unsaturated straight chain $C_5$-$C_{18}$ aliphatic radical and X represents —O—, —S—, —NH— or —CH$_2$— which comprises reacting a compound corresponding to the formula:

$$R-X-CH_2-\underset{\underset{R_2}{|}}{CH}-CH_2R_1 \quad (II)$$

in which R and X are as defined previously and $R_1$ and $R_2$ together represent an epoxy radical with ammonium carbamate to form a compound corresponding to the formula:

$$R-X-CH_2-CH(OH)-CH_2-NH-CO_2^- \quad (III)$$

$$R-X-CH_2-CH(OH)-CH_2-\overset{+}{N}H_3$$

in which R and X are as defined previously and thereafter heating the compound of formula (III) at a temperature and for a length of time sufficient to form the corresponding hydroxylated primary amine of formula (I).

2. A process of claim 1 wherein R is $C_5$-$C_{14}$ alkyl and X represents —O— or —S—.

3. A process of claim 1 wherein said ammonium carbamate is present in an amount of from about 1–10 moles of ammonium carbamate per mole of compound (II).

4. A process of claim 1 wherein the compound of formula (I) is 1-amino-3-decyloxy-2-propanol, the compound of formula (II) is (decyloxy)methyloxirane and the compound of formula (III) is 3-decyloxy-2-hydroxypropylcarbamic acid, 3-decyloxy-2-hydroxypropylammonium salt.

5. A process of claim 1 wherein the reaction of the compound of formula (II) with the compound of formula (III) is carried out in the presence of a lower alkanol having 1 to 6 carbon atoms.

6. A process of claim 5 wherein said alkanol is anhydrous methanol.

7. A process of claim 5 wherein said alkanol is present in an amount of from about 0.1 to 2.0 liters of alkanol per mole of ammonium carbamate.

8. A process of claim 1 wherein the compound of formula (III) is heated at a temperature of from about 50° C. to 100° C. for a period of time of from about 3 to 50 hours.

* * * * *